(12) United States Patent
Peppel

(10) Patent No.: US 7,510,545 B2
(45) Date of Patent: Mar. 31, 2009

(54) NEEDLELESS ACCESS PORT VALVES

(75) Inventor: Peter W. Peppel, Nazareth, PA (US)

(73) Assignee: B. Braun Medical Inc., Bethlehem, PA (US)

(*) Notice: Subject to any disclaimer, the term of this patent is extended or adjusted under 35 U.S.C. 154(b) by 530 days.

(21) Appl. No.: 11/055,285

(22) Filed: Feb. 9, 2005

(65) Prior Publication Data
US 2006/0178645 A1 Aug. 10, 2006

(51) Int. Cl.
A61M 5/14 (2006.01)
(52) U.S. Cl. ..................................... 604/256
(58) Field of Classification Search ............... 604/246, 604/249, 259, 256; 251/149, 149.8
See application file for complete search history.

(56) References Cited

U.S. PATENT DOCUMENTS

| | | | |
|---|---|---|---|
| 4,197,848 A | 4/1980 | Garrett et al. | |
| 4,535,819 A | 8/1985 | Atkinson et al. | |
| 4,765,588 A | 8/1988 | Atkinson | |
| 4,934,655 A | * 6/1990 | Blenkush et al. | 251/149.1 |
| 4,953,594 A | 9/1990 | Von Berg | |
| 5,006,114 A | 4/1991 | Rogers et al. | |
| 5,044,604 A | * 9/1991 | Topham et al. | 251/120 |
| 5,049,128 A | 9/1991 | Duquette | |
| 5,065,783 A | 11/1991 | Ogle, II | |
| 5,085,645 A | 2/1992 | Purdy et al. | |
| 5,104,389 A | 4/1992 | Deem et al. | |
| 5,108,380 A | 4/1992 | Herlitze et al. | |
| 5,147,333 A | 9/1992 | Raines | |
| 5,163,922 A | 11/1992 | McElveen, Jr. et al. | |
| 5,203,775 A | 4/1993 | Frank et al. | |
| 5,230,706 A | 7/1993 | Duquette | |
| 5,242,393 A | 9/1993 | Brimhall et al. | |
| 5,242,423 A | 9/1993 | Goodsir et al. | |
| 5,251,873 A | 10/1993 | Atkinson et al. | |
| 5,269,771 A | 12/1993 | Thomas et al. | |
| 5,281,206 A | 1/1994 | Lopez | |
| 5,289,849 A | 3/1994 | Paradis | |
| 5,330,450 A | 7/1994 | Lopez | |
| 5,344,414 A | 9/1994 | Lopez et al. | |
| 5,353,837 A | 10/1994 | Faust | |
| 5,360,413 A | 11/1994 | Leason et al. | |
| 5,380,306 A | 1/1995 | Brinon | |
| 5,390,898 A | 2/1995 | Smedley et al. | |
| 5,395,348 A | 3/1995 | Ryan | |
| 5,401,245 A | 3/1995 | Haining | |
| 5,423,791 A | 6/1995 | Bartlett | |
| 5,425,465 A | 6/1995 | Healy | |
| 5,439,451 A | * 8/1995 | Collinson et al. | 604/247 |

(Continued)

Primary Examiner—Nicholas D Lucchesi
Assistant Examiner—Aarti Bhatia
(74) Attorney, Agent, or Firm—Klein, O'Neill & Singh, LLP

(57) ABSTRACT

Needleless access port valves are generally discussed herein with particular discussions extended to needleless access port valves having a pliant valve body configured to expand to accommodate a plug when the same is pushed by a syringe or a medical implement and contract when the syringe or medical implement is removed to return the plug to its original position. The plug can move distally and tilt when inside the pliant valve body or remain generally upright when its top surface incorporates flow channels. Interior baffles are included for fluid flow through the interior cavity of the valve. The baffles can vary in shape, number, contour, and can include a ramp.

25 Claims, 8 Drawing Sheets

U.S. PATENT DOCUMENTS

| | | | |
|---|---|---|---|
| 5,441,487 A | 8/1995 | Vedder | |
| 5,462,255 A | 10/1995 | Rosen et al. | |
| 5,466,219 A | 11/1995 | Lynn et al. | |
| 5,509,433 A | 4/1996 | Paradis | |
| 5,509,912 A | 4/1996 | Vaillancourt et al. | |
| 5,533,983 A | 7/1996 | Haining | |
| 5,535,771 A * | 7/1996 | Purdy et al. | 137/15.01 |
| 5,535,785 A | 7/1996 | Werge et al. | |
| 5,540,661 A | 7/1996 | Tomisaka et al. | |
| 5,549,577 A | 8/1996 | Siegel et al. | |
| 5,569,235 A | 10/1996 | Ross et al. | |
| 5,573,516 A | 11/1996 | Tyner | |
| 5,584,808 A | 12/1996 | Healy | |
| 5,616,129 A | 4/1997 | Mayer | |
| 5,620,434 A | 4/1997 | Brony | |
| 5,624,414 A | 4/1997 | Boettger | |
| 5,645,538 A | 7/1997 | Richmond | |
| 5,674,206 A | 10/1997 | Allton et al. | |
| 5,676,346 A | 10/1997 | Leinsing | |
| 5,685,866 A | 11/1997 | Lopez | |
| 5,690,612 A | 11/1997 | Lopez et al. | |
| 5,694,686 A | 12/1997 | Lopez | |
| 5,695,466 A | 12/1997 | Lopez et al. | |
| 5,699,821 A | 12/1997 | Paradis | |
| 5,700,248 A | 12/1997 | Lopez | |
| 5,730,418 A | 3/1998 | Feith et al. | |
| 5,738,663 A | 4/1998 | Lopez | |
| 5,743,894 A | 4/1998 | Swisher | |
| 5,749,861 A * | 5/1998 | Guala et al. | 604/249 |
| 5,776,113 A | 7/1998 | Daugherty et al. | |
| 5,782,816 A | 7/1998 | Werschmidt et al. | |
| 5,785,693 A | 7/1998 | Haining | |
| 5,788,215 A | 8/1998 | Ryan | |
| 5,806,551 A * | 9/1998 | Meloul et al. | 137/1 |
| 5,806,831 A | 9/1998 | Paradis | |
| 5,810,768 A | 9/1998 | Lopez | |
| 5,810,792 A | 9/1998 | Fangrow, Jr. et al. | |
| 5,810,793 A | 9/1998 | Boettger | |
| 5,839,715 A | 11/1998 | Leinsing | |
| 5,848,994 A | 12/1998 | Richmond | |
| 5,873,862 A | 2/1999 | Lopez | |
| 5,921,264 A | 7/1999 | Paradis | |
| 5,921,419 A | 7/1999 | Niedospial, Jr. et al. | |
| 5,928,204 A | 7/1999 | Lopez | |
| 5,957,898 A | 9/1999 | Jepson et al. | |
| 5,967,490 A | 10/1999 | Pike | |
| 5,971,950 A | 10/1999 | Lopez et al. | |
| 6,019,748 A | 2/2000 | Lopez | |
| 6,029,946 A * | 2/2000 | Doyle | 251/149.1 |
| 6,036,171 A | 3/2000 | Weinheimer et al. | |
| 6,039,302 A | 3/2000 | Cote, Sr. et al. | |
| 6,045,534 A | 4/2000 | Jacobsen et al. | |
| 6,063,062 A | 5/2000 | Paradis | |
| 6,068,011 A | 5/2000 | Paradis | |
| 6,083,194 A | 7/2000 | Lopez | |
| 6,106,502 A | 8/2000 | Richmond | |
| 6,113,068 A | 9/2000 | Ryan | |
| 6,117,114 A | 9/2000 | Paradis | |
| 6,127,320 A | 10/2000 | van Ooij et al. | |
| 6,132,403 A | 10/2000 | Lopez | |
| 6,132,404 A | 10/2000 | Lopez | |
| 6,142,446 A | 11/2000 | Leinsing | |
| 6,152,900 A | 11/2000 | Mayer | |
| 6,168,137 B1 | 1/2001 | Paradis | |
| 6,170,800 B1 | 1/2001 | Meloul et al. | |
| 6,171,287 B1 | 1/2001 | Lynn et al. | |
| 6,189,859 B1 | 2/2001 | Rohrbough et al. | |
| 6,228,069 B1 | 5/2001 | Barth et al. | |
| 6,245,048 B1 | 6/2001 | Fangrow, Jr. et al. | |
| 6,245,056 B1 | 6/2001 | Walker et al. | |
| 6,261,268 B1 | 7/2001 | Mayer | |
| 6,273,869 B1 | 8/2001 | Vaillancourt | |
| 6,290,206 B1 | 9/2001 | Doyle | |
| 6,290,688 B1 | 9/2001 | Lopez et al. | |
| 6,299,131 B1 | 10/2001 | Ryan | |
| 6,299,132 B1 | 10/2001 | Weinheimer et al. | |
| 6,325,782 B1 | 12/2001 | Lopez | |
| 6,344,033 B1 | 2/2002 | Jepson et al. | |
| 6,364,869 B1 | 4/2002 | Bonaldo | |
| 6,428,520 B1 | 8/2002 | Lopez et al. | |
| 6,482,188 B1 | 11/2002 | Rogers et al. | |
| 6,491,668 B1 | 12/2002 | Paradis | |
| 6,541,802 B2 | 4/2003 | Doyle | |
| 6,572,591 B2 | 6/2003 | Mayer | |
| 6,572,592 B1 | 6/2003 | Lopez | |
| 6,585,229 B2 | 7/2003 | Cote, Sr. et al. | |
| 6,599,273 B1 | 7/2003 | Lopez | |
| 6,616,627 B2 | 9/2003 | Willis et al. | |
| 6,626,418 B2 | 9/2003 | Kiehne | |
| 6,635,044 B2 | 10/2003 | Lopez | |
| 6,641,561 B1 | 11/2003 | Hill et al. | |
| 6,645,170 B2 | 11/2003 | Landau | |
| 6,669,673 B2 | 12/2003 | Lopez | |
| 6,669,681 B2 | 12/2003 | Jepson et al. | |
| 6,682,509 B2 | 1/2004 | Lopez | |
| 6,695,817 B1 | 2/2004 | Fangrow, Jr. | |
| 6,706,022 B1 | 3/2004 | Leinsing et al. | |
| 6,755,391 B2 | 6/2004 | Newton et al. | |
| 6,758,833 B2 | 7/2004 | Lopez | |
| 6,802,490 B2 | 10/2004 | Leinsing et al. | |
| 6,840,501 B2 | 1/2005 | Doyle | |
| 6,855,138 B2 | 2/2005 | Tsai | |
| 6,869,426 B2 | 3/2005 | Ganem | |
| 6,871,838 B2 | 3/2005 | Raines et al. | |
| 7,357,792 B2 * | 4/2008 | Newton et al. | 604/244 |
| 7,396,348 B2 * | 7/2008 | Newton et al. | 604/256 |
| 2003/0050610 A1 * | 3/2003 | Newton et al. | 604/256 |
| 2004/0173556 A1 * | 9/2004 | Smolko et al. | 215/11.5 |

* cited by examiner

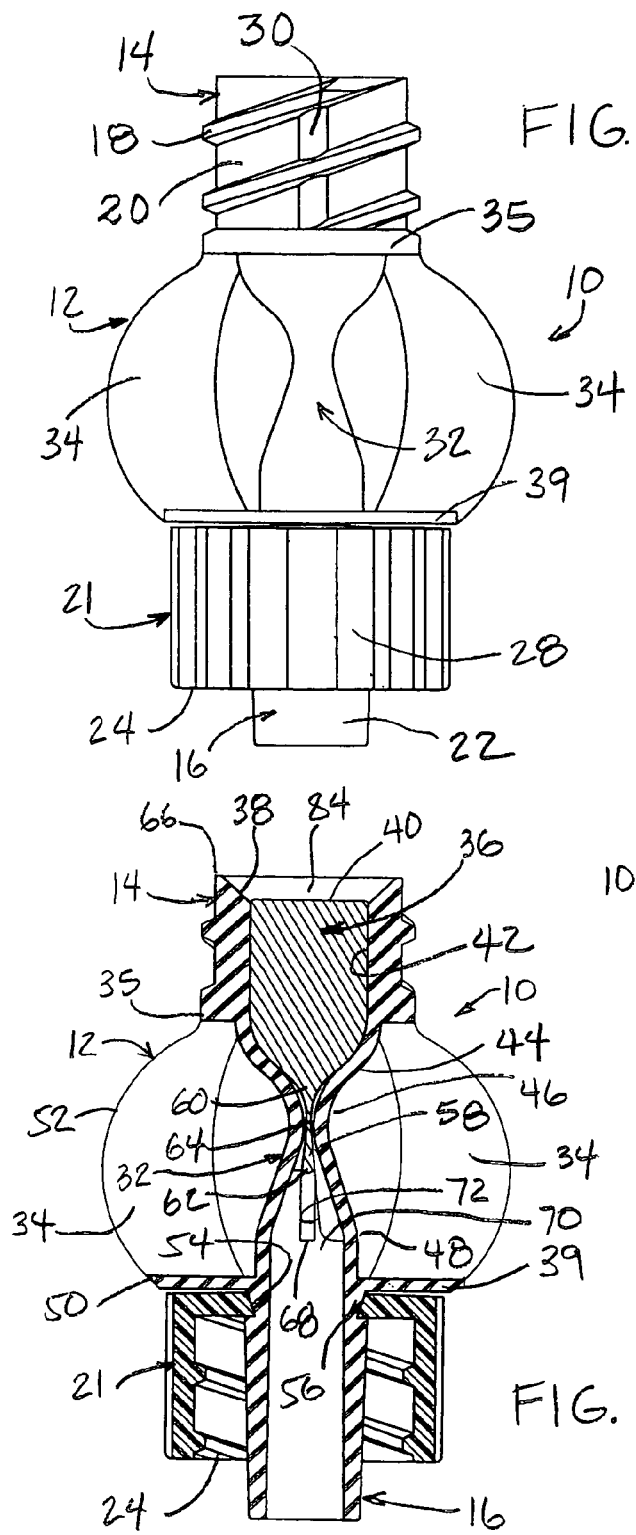
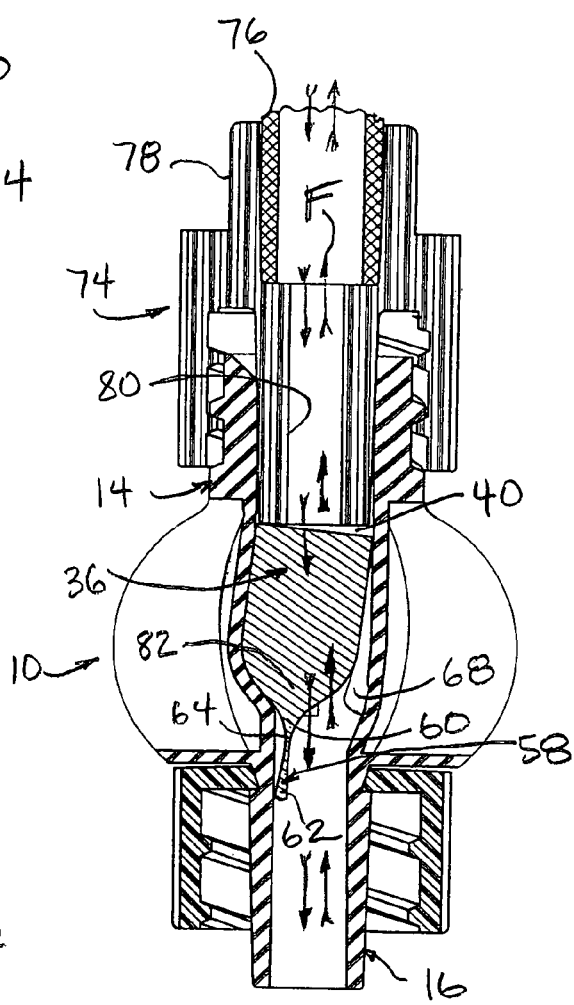
FIG. 1
FIG. 2
FIG. 3

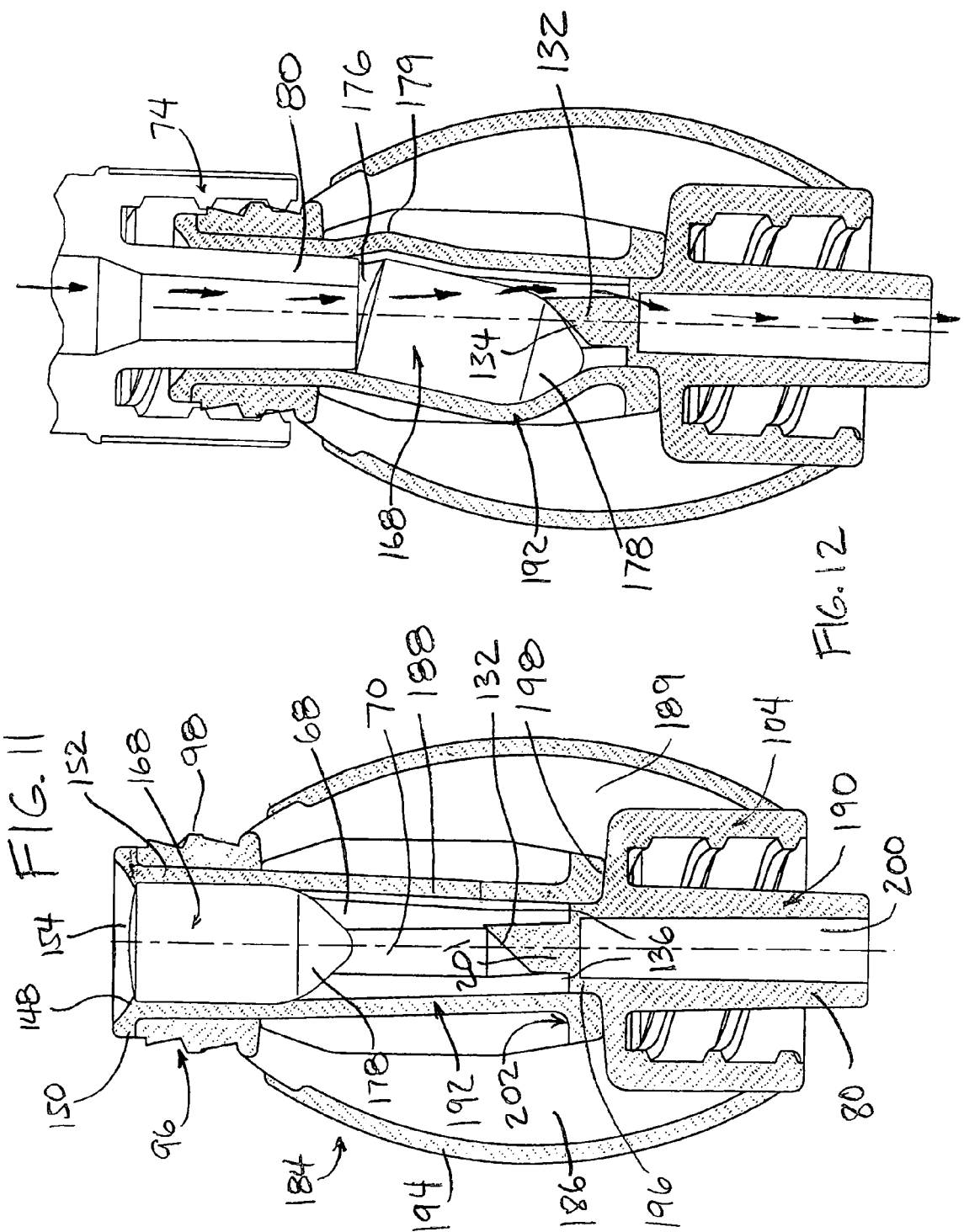

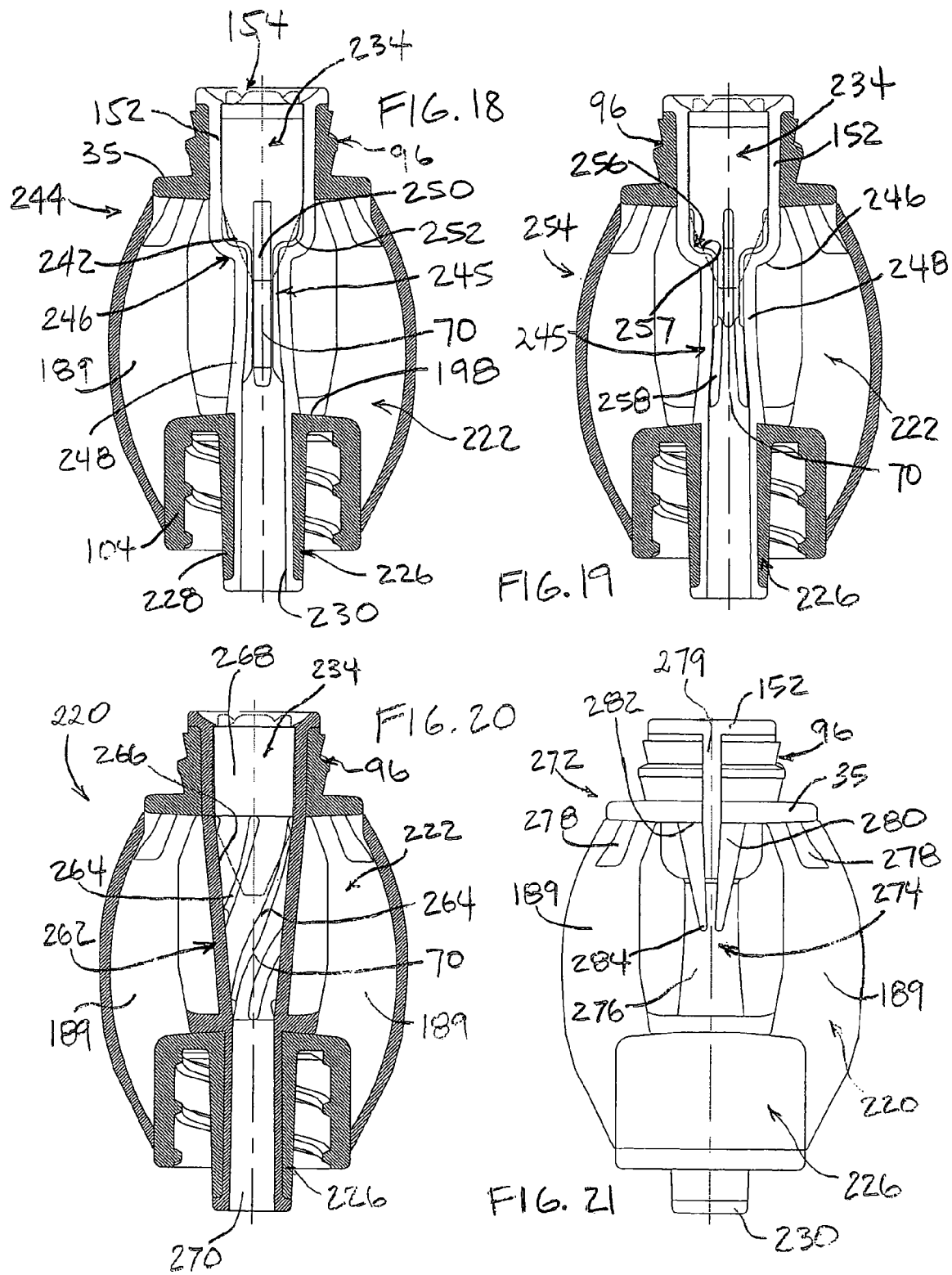

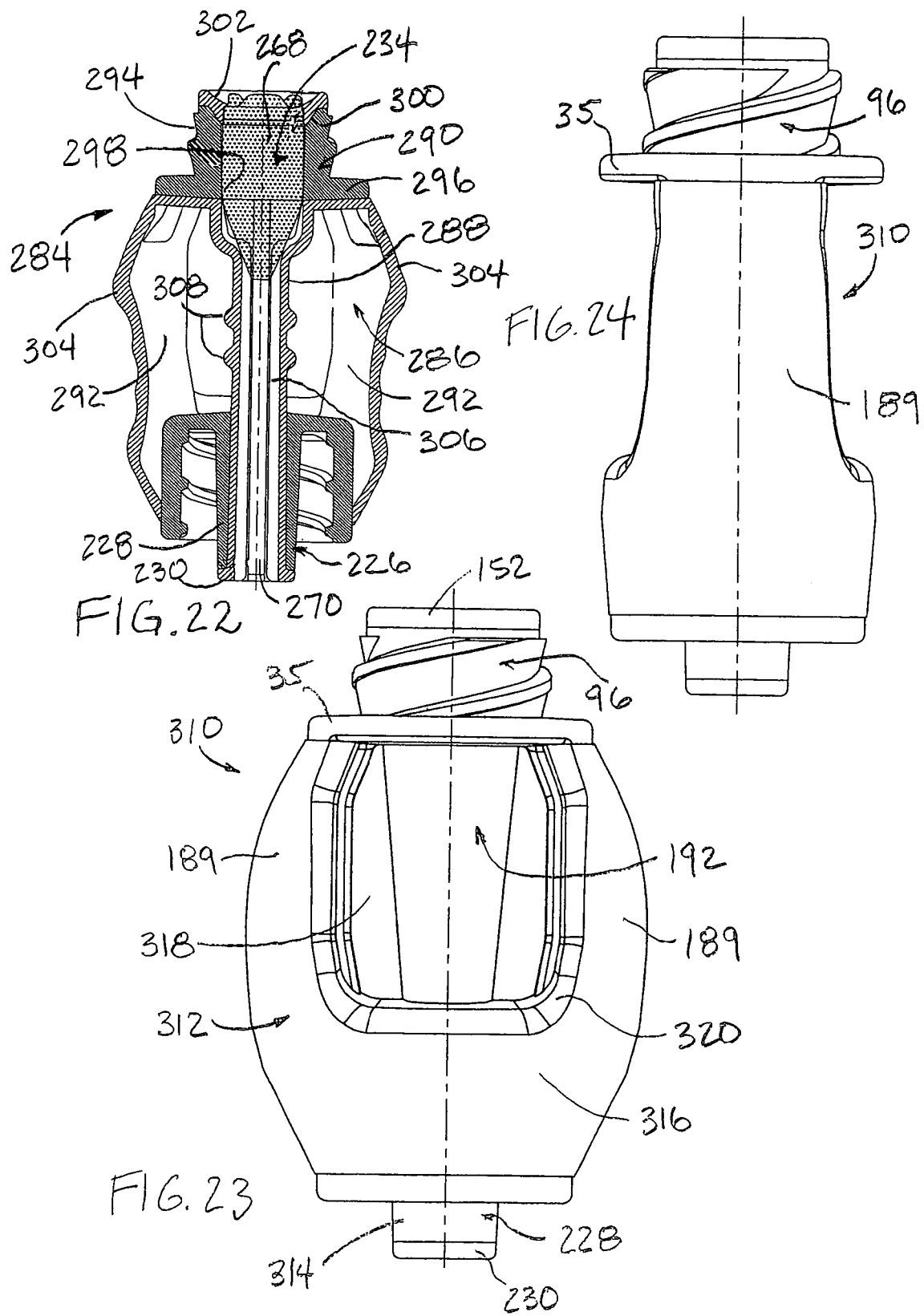

NEEDLELESS ACCESS PORT VALVES

Needleless access port valves are generally discussed herein with particular discussions extended to needleless access port valves comprising a pliant valve body for interacting with a plug.

BACKGROUND

Needleless access port valves are widely used in the medical industry for accessing an IV line and/or the internals of a patient or subject. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a needleless access port valve comprising a valve body, an inlet, an outlet, a main channel about a central axis between the inlet and the outlet, and a plug disposed in the main channel and movable inside the main channel between a first position and a second position for controlling fluid communication between the inlet and the outlet, the plug comprising an upper end and a lower end comprising a tapered section; wherein the valve body comprises a flexible wall flexibly bending inwardly towards the central axis when the plug is in the first position; and wherein the flexible wall flexibly bending outwardly away from the central axis and contacting the tapered section when the plug is in the second position.

In another aspect of the present invention, a needleless access port valve is provided comprising a valve body defining an interior cavity, an inlet, an outlet, a plug disposed in the interior cavity of the valve body and movable within the interior cavity between a first position and a second position for controlling fluid communication between the inlet and the outlet, and a valve body section comprising a flexible wall; wherein the flexible wall expands outwardly to accommodate the plug when the plug moves to the second position.

In yet another aspect of the present invention, there is provided a needleless access port valve comprising a valve body defining an interior cavity, an inlet, an outlet, a plug disposed in the interior cavity of the valve body and movable within the interior cavity between a first position and a second position for controlling fluid communication between the inlet and the outlet, wherein the wall contracts to move the plug from the second position to the first position.

BRIEF DESCRIPTION OF THE DRAWINGS

These and other features and advantages of the present invention will become appreciated as the same becomes better understood with reference to the specification, claims and appended drawings wherein:

FIG. 1 is a semi-schematic side view of an exemplary needleless access port valve provided in accordance with aspects of the present invention;

FIG. 2 is a semi-schematic cross-sectional side view of the valve of FIG. 1 in a ready to use or first position;

FIG. 3 is a semi-schematic cross-sectional side view of the valve of FIG. 1 in use with a plug in a second position;

FIG. 11 is a semi-schematic cross-sectional side view of another alternative needleless access port valve provided in accordance with aspects of the present invention;

FIG. 12 is a semi-schematic cross-sectional side view of the valve of FIG. 11 in a use position;

FIG. 18 is a semi-schematic cross-sectional side view of another alternative needleless access port valve provided in accordance with aspects of the present invention, shown with a plug in phantom;

FIG. 19 is a semi-schematic cross-sectional side view of still yet another alternative needleless access port valve provided in accordance with aspects of the present invention, shown with a plug in phantom;

FIG. 20 is a semi-schematic cross-sectional side view of yet another alternative needleless access port valve provided in accordance with aspects of the present invention, shown with a plug in phantom;

FIG. 21 is a semi-schematic side view of yet another alternative needleless access port valve provided in accordance with aspects of the present invention, FIG. 22 is a semi-schematic cross-sectional side view of yet another alternative needleless access port valve provided in accordance with aspects of the present invention;

FIG. 23 is a semi-schematic side view still yet another alternative needleless access port valve provided in accordance with aspects of the present invention; and FIG. 24 is a semi-schematic side view of the valve of FIG. 23 from a different plane.

DETAILED DESCRIPTION

Figure 4:
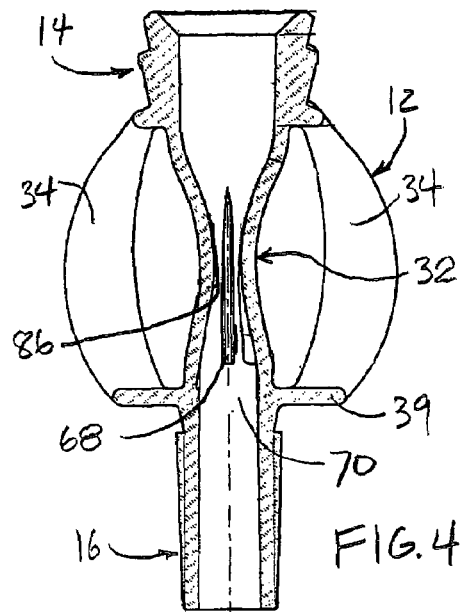
FIG. 4 is a semi-schematic cross-sectional side view of a component of the valve of FIG. 1, which includes the inlet and the outlet.

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Referring now to FIG. 1, there is shown a first exemplary needleless access or injection port valve provided in accordance with aspects of the present invention, which is generally designated 10. The needleless access port valve 10 (herein "valve") comprises a valve housing 12 having an inlet 14 and an outlet 16. The inlet 14 comprises a female luer connector for receiving a first medical implement and has external threads 18 around the upper exterior surface 20 of the valve housing 12. The external threads 18 are configured for threaded engagement with corresponding threads on the first medical implement.

The outlet 16 comprises a male luer connector 22 for mating engagement with a second medical implement. A shroud or collar 21 comprising internal threads 24 is positioned co-axially with the male luer connector 22 for threading engagement with corresponding threads on the second medical implement. The term medical implement is used broadly to denote any number of devices useable with the valve such as a syringe, an IV set, a Y-connector, a tubing adaptor, a catheter etc. Optionally, the external threads 18 at the inlet or the internal threads 24 on the collar 21 or both may be eliminated, which makes the valve 10 a luer-slip type valve. Still alternatively, the threads may be retained and a medical implement with a luer slip used. Also optionally, a plurality of raised ridges or bumps 26 for facilitating gripping by a user may be incorporated around the exterior surface 28 of the collar 21.

One or more interference rib 30 may be incorporated at the inlet section adjacent the external threads 18. In one exemplary embodiment, the one or more interference ribs 30 comprise a raised bump incorporated on the surface 20 of the inlet. In a preferred embodiment, two interference ribs 30 are equally spaced apart around the periphery of the inlet 14 and each comprises a length that extends parallel with the lengthwise direction of the valve body or valve core 32. The interference ribs 30 are configured to provide increased friction between the inlet and a mating medical implement to enhance the connection therebetween.

Two guide ribs or guide columns 34 adjacent the valve body 32 are incorporated. The two guide ribs 34 are each attached to an upper or first flange 35 adjacent the external threads 18 and a second or lower flange 39 adjacent the collar 21. The guide ribs 34 are adapted to maintain a gap or dimension defined by the space between the upper flange 35 and the lower flange 39 to be substantially fixed when the valve 10 is in the position shown (i.e., first position) and when the valve is in use (i.e., second position), as discussed further below. As is readily apparent to a person of ordinary skill in the art, three or more guide ribs or columns 34 may be incorporated in an evenly-spaced apart configuration around the valve body 32. In one exemplary embodiment, the ribs 34 are generally flat and each incorporates a shape resembling a main sail. Obviously, the shape of the ribs 34 can vary provided they incorporate sufficient structural rigidity to withstand normal compression and tension forces generated when the valve 10 is in use to maintain a substantially constant gap defined by the space between the upper and the lower flanges 36, 39. By substantial, the gap between the upper flange and the lower flange should not deviate by more than ±25% and preferably more than 5% when undergoing compression or tension during normal use.

Referring now to FIG. 2, a semi-schematic cross-sectional side view of the valve 10 of FIG. 1 is shown. As discernable from the different cross-hatches, the valve comprises three separate components, namely the plug 36, the collar 21, and the valve housing 12. The valve housing 12 in turn includes the valve body 32, the inlet 14, the outlet 16, and the two guide ribs 34. In one exemplary embodiment, the valve housing 12 is integrally formed from a thermoplastic elastomer (TPE). In one exemplary embodiment, the TPE is a member of the copolyamide (COPA) family of thermoplastic elastomers. In a preferred embodiment, the COPA is copolyamide thermoplastic elastomer having a commercial trade name PEBAX®. However, other TPEs may also be used to make the valve housing 12, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics.

In one exemplary embodiment, the valve housing 12 is made by injection molding. The preferred TPE selected should have good to excellent memory property for expanding and returning to its original state In an exemplary embodiment, the inlet 14 is provided with a sloped or tapered entrance 38 for facilitating insertion of a medical implement and for wiping the upper surface 40 of the plug 36. The upper interior surface 42 of the inlet 14 is preferably of a standard luer taper and is configured to seal against the exterior surface of the plug 36 via a standard Luer to Luer taper engagement.

The hour-glass-like valve body or valve core 32 comprises an upper bowl section 44 formed by tapering the valve body inwardly from the upper interior surface 42 towards the axial lengthwise center of the valve body 32. In an exemplary embodiment, the amount of taper to form the upper bowl section is such that the upper bowl section 44 reduces into a funnel 46 at approximately a mid-point between the upper flange 35 and the lower flange 39, similar to an hour-glass. In a preferred embodiment, the taper, and hence the funnel 46, is formed closer to the upper flange 35 than the lower flange 39.

The lower bowl section 48 extends from the funnel 46 into the outlet 16 of the valve housing 12. In one exemplary embodiment, the interior diameter of the valve body at the upper flange 35 is larger in diameter than the interior diameter at the lower flange 39. Thus, the lower bowl section 44 has a more gradual taper than the upper bowl section 48. However, the valve body 32 may incorporate symmetrical upper and lower bowl sections or other configurations without deviating from the spirit and scope of the present invention provided the valve body resembles an hour-glass.

The lower flange 39 is generally circular in configuration and, in one exemplary embodiment, incorporates a tapered or arced end edge 50 of similar angle or curvature as the exterior curvature 52 of the guide ribs 34. A groove or indentation 54 just distal or below the lower flange 39 is incorporated for mating engagement with the collar 21. In an exemplary embodiment, the groove 54 is formed, extending distally from the lower flange 39, with a radially inwardly taper. The groove 54 is configured to mate with a central opening 56 on the collar 21, which has a corresponding similar taper as the groove 54. The collar 21 is placed in mating engagement with the groove 54 by pushing the outlet 16 through the central opening 56 of the collar 21 until the perimeter of the central opening 56 engages the groove 54. Because the outlet 16 is made from a pliable TPE material, the outlet nozzle will flex or give to permit the collar 21 to be pushed proximally to engage the groove 54.

In an exemplary embodiment, the plug 36 and the collar 21 are both made from a rigid thermoplastic. In a preferred embodiment, the plug 36 is made from a polycarbonate material and the collar is also made from polycarbonate. However, other thermoplastics may be used to make the plug 36 and the collar 21, including such thermoplastics Nylons, PVC, ABS, styrene acrylonitrile (SAN), acrylonitrile styrene acrylate (ASA), poly-phenylene oxide (PPO), polystyrene, and their blends.

As can be seen in FIGS. 2 and 3, the plug 36 incorporates a tail 58 at the end opposite the top surface 40 of the plug. The tail 58 is preferably integrally molded to the plug and comprises an upper tail section 60 having an upper cross-sectional area, a lower tail section 62 having a lower cross-sectional area, and a middle tail section 64 having a middle cross-sectional area. The middle cross-sectional area is preferably smaller than the upper and the lower cross-sectional areas and the lower cross-section area is preferably smaller than the upper cross-sectional area. As such, the tail 58 comprises a configuration that also resembles an hour-glass, similar to the valve body 32. Preferably in the ready to use position or first position, the middle tail section 64 and the funnel or middle section 46 of the valve body 32 are coincidence of one another such that the middle section 46 of the valve body grips the middle section 64 of the tail to thereby hold the plug 36 in place inside the valve body.

In one exemplary embodiment, the plug 36 and the tail 58 are dimensioned such that when the valve body 32 grips the tail 58, the top surface 40 of the plug is positioned just below the top perimeter 66 of the inlet 14. More preferably, the plug and the tail are so dimensioned such that the top surface 40 of the plug is near the transition between the sloped entrance 38 and the upper interior surface 42.

A plurality of baffles 68 are incorporated in the interior cavity 70 of the valve body 32. As further discussed below, the plurality of baffles 68 are configured to tilt the plug 36 to provide clearance between the top surface 40 of the plug and a medical implement (See, e.g., FIG. 3) to provide a gap for fluid flow between the inlet 14 and the outlet 16. The baffles 68 each resembles a sloped ramp with the ramp inclining further away from interior surface of the valve body, i.e., more radially inwardly, as the ramp extends in the direction of the inlet 14 towards the outlet 16. In an exemplary embodiment and when in the first position, the forward surface 72 of each ramp 68 is substantially perpendicular to the top surface 40 of the plug 36. In an exemplary embodiment, the plurality of baffles 68 are incorporated asymmetrically such that the baffles are non-uniformly spaced apart inside the interior cavity 70 of the valve body 32. In a preferred embodiment, three baffles 68 are incorporated in the interior cavity of the valve body 32 with a middle baffle spaced apart from two adjacent baffles by 90 degrees. Thus, in a preferred embodiment, the three baffles occupy 270 degrees of the interior cavity of the valve body. However, two or more than three baffles may be incorporated inside the valve and the baffles may occupy from about 30 degrees to about 300 degrees of the interior cavity of the valve body. Still alternatively, even spaced apart ribs may be used provided at least one of the ribs have varying bulk or taper to allow the plug to tilt.

As discussed above, the plug 36 is preferably made from a rigid thermoplastic. In a preferred embodiment, the plug and the interior cavity of the inlet port incorporate a standard Luer to Luer engagement. In an exemplary embodiment, a lubricant, such as medical grade silicone, should be used to coat the surface of the plug 36 before inserting the plug into the inlet of the valve body 32 to facilitate assembly.

Turning now to FIG. 3, a medical implement 74 comprising a tubing 76 and a male luer tubing adapter 78 is shown connected to the inlet 14 of the valve 10 of FIG. 2. The male luer of the tubing adapter 78 pushes the plug 36 from the first position (FIG. 2) to a second position (FIG. 3), in which the top surface 40 of the plug is further spaced-apart from the top perimeter 66 of the inlet 14. In moving from the first position to the second position, the lower base section 82 of the plug 36 pushes down on the upper bowl section 44 of the valve body 32 and expands the upper bowl section 44 and the adjoining mid or funnel section 46 of the valve body 32. Because the valve housing 12 and the valve body 32 are made from a TPE material, the elasticity of the material permits it to expand to accommodate the plug 36.

As the wall of the valve body 32 expands by the advancing plug, the length of the valve body between the first flange 35 and the second flange 39 tends to decrease. However, as discussed above, the guide ribs 34 counteract the valve body's tendency to decrease. The guide ribs 34, with bulkier or heavier built, require higher compressive force to shorten or compress than the force generated by the expansion of the valve body caused by the medical implement acting on the plug 34. In addition, the guide ribs 34 are configured to resist torsional forces generated by the male luer adapter 78 rotating and engaging the threads 18 at the valve inlet 14.

As shown in FIG. 3, the plug 36 tilts at angle when it moves from the first position to the second position, as can be seen from the position of the tail 58 relative to the center of the interior cavity 70 of the valve body 32 and from the gap or space between the male luer 80 of the medical implement 74 and the top surface 40 of the plug 36. The tilting is caused by the plug 36 contacting the asymmetrically placed plurality of baffles 68 located inside the interior cavity 70 of the valve body 32. The plug 36, and more particularly the tail 58, tilts to the side of the cavity 70 that does not incorporate a baffle 68, or if an even number of baffles are incorporated, to the side with the smallest or more shallow baffle.

The tilting of the plug 36 provides a clearance or fluid opening for fluid flow flowing from either the medical implement 74 to and through the valve 10, or from a source downstream of the valve 10, such as from a patient, to flow through the valve 10 towards the medical implement 74. Assuming a fluid flow in the direction of the medical implement 74 towards the valve 10, the fluid F will flow as follows: the stream of fluid flows F out of the male luer 80, is dispersed in various directions when it hits the top surface 40 of the plug, the dispersed streams flow between the plug and the internal surface the valve body 32 in between the plurality of baffles 68, the streams are then, to some extent, recombined and the single combined stream exits the outlet 16.

When the medical implement 74 is removed from the inlet 14, the downward force applied on the plug 36 to expand the valve body 32 is released and the valve body 32 recoils to its first position (FIG. 2). The contracting force generated by the valve body 32 in returning to its first position imparts a pair of component forces along the tapered lower base section 82 of the plug 36 and pushes the plug 36 proximally or upwardly towards the inlet opening 84. The upward travel of the plug 36 is delimited by the interactions between the funnel section 46 of the valve body 32 and the funnel section or mid-section 64 of the tail 58. More particularly, as the valve body 32 contracts and returns to its first position, it reverts back to the hour-glass configuration. In the process, the mid-section or funnel 46 of the valve body 32 forms around the mid-section 64 of the tail 58 to hold the tail, and therefore the plug 36, within the desired first position. In one exemplary embodiment, the funnel 46 of the valve body 32 is in a contact engagement with the mid-section of the tail 58. In an alternative embodiment, the two mid-sections may have a loose fit.

As is readily apparent to a person of ordinary skill in the art, the valve 10 may be modified without deviating from the spirit and scope of the present invention. For example, the plug 36 may incorporate ridges or ribs along the upper top surface 40 to provide clearance for incoming fluid flow from the medical implement 74 without having to tilt the plug 36. In connection therewith, the baffles 68 may be incorporated uniformly or symmetrically within the interior cavity of the valve body and provide flow channels. Other changes may be incorporated or practiced including changing the length or dimensions of various components and adding colors for aesthetic appeal, to name a few.

In yet another alternative embodiment, the valve housing 12 may be made from a two-part self-lube liquid silicone rubber rather than from a TPE material. The two-part self-lube silicone rubber is commercially available from Nusil Silicone Technology of Santa Barbara, Calif. Various aspects of the self-lube liquid silicone rubber are described in Ser. No. 10/407,001, filed Apr. 3, 2003, the contents of which are expressly incorporated herein by reference as if set forth in full. In the embodiment in which the valve housing 12 is made from the self-lube liquid silicone material, the plug 36 may be inserted into the inlet 14 without necessarily applying medical grade silicone to the exterior surface of the plug. In another alternative embodiment, only the plug is made from a two-part self-lubricating silicone rubber and the valve body made from a pliable material, such as a TPE material. When a two-part liquid silicone rubber is used, a durometer range of about 50 to about 65 is preferred.

Referring now to FIG. 4, a cross-sectional side view of the valve housing 12 without the plug 36 and without the collar 21 is shown. FIG. 4 shows various features of the integrally formed valve housing, which as discussed above include the inlet 14, the guide ribs or columns 34, the valve body 32, the lower flange 39, the outlet 16, and the plurality of baffles 68. While these components are preferably integrally formed, it will be readily apparent to a person of ordinary skill in the art that the valve housing 12 may be constructed from separately molded components. For example, the guide ribs 34 may be constructed from a rigid plastic and may be over-molded or co-molded with the valve body 32, the inlet 14, and the outlet 16.

In one exemplary embodiment, a shortened baffle 86 is incorporated in the interior cavity 70 of the valve body 32. The shortened baffle 86, as the name implies, is shorter in length than the plurality of baffles 68 incorporated inside the valve body 32 for tilting the plug 36 and for providing flow channels or paths for the flow of fluid. The shortened baffle 86 is incorporated to provide flow paths for fluid flow around the upper section of the plug 36 yet sufficiently short to permit the plug to tilt by providing a gap or a space in the region below the shortened baffle.

Figure 5:
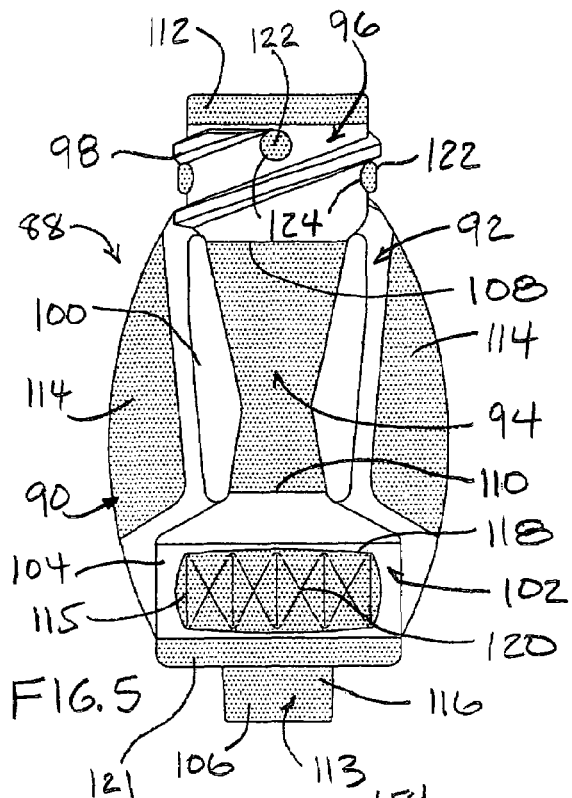
FIG. 5 is a semi-schematic side view of an alternative needleless access port valve provided in accordance with aspects of the present invention.

FIG. 5 is a semi-schematic side view of an alternative valve 88 provided in accordance with aspects of the present invention. Like the first embodiment, the valve 88 in the present embodiment incorporates a valve housing 90 that includes a rigid thermoplastic and a pliable valve body 94. In one exemplary embodiment, the valve 88 incorporates a rigid thermoplastic body skeleton or frame 92 made from injection molding methods and a pliable valve body 94 over molded to the frame 92. In one exemplary embodiment, the rigid thermoplastic frame and the pliable valve body are made from similar materials as those described above with reference to the first embodiment.

In one exemplary embodiment, the frame 92 comprises an inlet section 96 having external luer threads 98, guide ribs or guide columns 100, and an outlet section 102 comprising an outlet shroud 104 comprising internal threads (not shown, See FIG. 6) and a male outlet stub 106 over molded in the same material as the valve body 94 to from the luer outlet 113, as further discussed below. The guide ribs 100 on the frame 92 are configured to maintain a substantially fixed gap or space between an upper ledge 108 and a lower ledge 110 of the frame when the valve 88 is both in use and not in use, as further discussed below.

In one exemplary embodiment, the pliable valve body 90 comprises an inlet section 112, which forms a liner for the inlet section 96 of the shell 92, the valve body 94, a pair of gripping fins 114, a pair of gripping pads 115, and an outlet liner 116, which surrounds the outlet stub 106 on the frame 92 to form the outlet 113. Although the valve body 90 is preferably made from a single over-molded step, in one exemplary embodiment, the pair of gripping fins 114 and the pair of gripping pads 115 may be separately formed or molded to the frame 92. In the separately formed embodiment, the pair of gripping fins 114 may be over-molded to the guide ribs 100 and held thereto via anchor holes, and the pair of gripping pads 115 may be over molded to a pair of recessed receiving slots 118 formed on the exterior surface of the outlet shroud 104, as further discussed below. Optional projections or ridges 120 may be incorporated on the gripping pads 115 to facilitate gripping the valve 88 when engaging or disengaging the valve with a first and/or a second medical implement (not shown). Also optionally, a plurality of friction nubs 122 may be incorporated proximate the inlet luer threads 98 by over-molding a TPE material into a plurality of recessed receptacles 124 located at the upper inlet section 96 of the rigid body skeleton 92. Still optionally, a perimeter flange 121 may be incorporated at the distal end of the outlet section 102 for gripping and for minimizing sharp corners.

Figure 6:
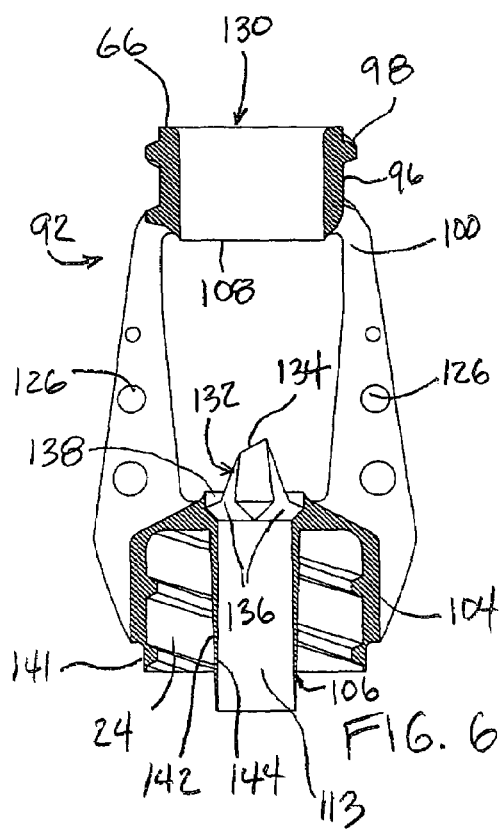
FIG. 6 is a semi-schematic cross-sectional side view of a component of the valve of FIG. 5.

Referring now to FIG. 6, a semi-schematic cross-sectional side view of the rigid skeleton or frame 92 is shown in accordance with aspects of the present invention. The frame 92 includes a pair of guide ribs 100 attached to the inlet section 96 and the outlet shroud 104. The guide ribs 100 incorporate a plurality of anchor holes 126 for the pliable gripping fins 114 to anchor against. The anchor holes 126 allow the anchor joints 128 (FIG. 7) to penetrate when over-molding the gripping fins 114. The inlet section 96 includes an inlet opening 130 and the upper ledge 108. The upper ledge 108 defines a lower section of the inlet. The inlet section 96 should be sized so that when the pliable valve body 94 is over-molded thereto, the final inlet size is appropriate to receive a medical implement. In a preferred embodiment, the final inlet size is a standard luer taper.

A deflection post 132 is centrally incorporated on the outlet shroud 104. The deflection post 132 comprises a semi-frustoconical shape nose section comprising a slanted opening 134 configured to tilt a plug when the same is pushed by a medical implement against the post, as further discussed below. The deflection post 132 is attached to the outlet shroud 104 by a pair of thin profile ribs 136. Thus, the annular opening 138 of the outlet shroud 104 for passing flow therethrough is divided into two segmented flow channels or paths due to the presence or location of the deflection post 132 and the pair of thin profile ribs 136. Accordingly, when fluid flows through the valve, the flow divides in two streams and the two streams flow through the two segmented openings, as further discussed below, before exiting the outlet 113. The deflection post 132 is preferably solid and is not configured to pass fluid therethrough.

An elongated stub 106 is integrally formed with the outlet shroud 104. The stub or port 106 has a slight taper on both its exterior surface 142 and its interior surface 144. The taper on the exterior surface 142 is preferably greater, i.e., a larger angle, than the taper on the interior surface 144. In one exemplary embodiment, the interior taper on the interior surface 144 is the same taper as a luer taper. The elongated port 106 and the port liner 116 of the pliable body 94 (FIG. 7) together make up a standard male luer connector outlet. In one exemplary embodiment, threads 24 are incorporated on the interior surface of the outlet shroud 104 for threaded engagement with a medical implement. A recessed perimeter edge 141 is incorporated at the distal edge of the outlet shroud 104 for receiving the over-molded perimeter flange 121 (FIGS. 5 and 7).

Figure 7:
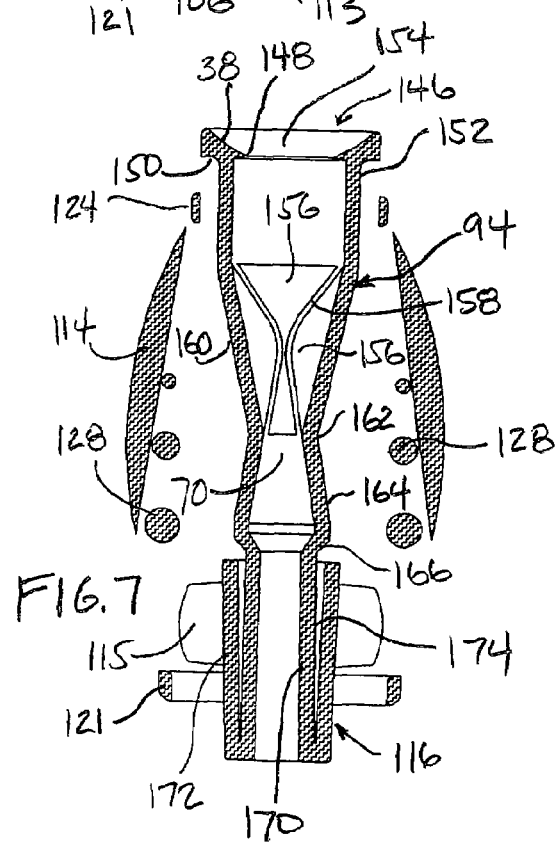
FIG. 7 is a semi-schematic cross-sectional side view of another component of the valve of FIG. 5.

Referring now to FIG. 7, a semi-schematic cross-sectional side view of the pliable body 94 is shown provided in accordance with aspects of the present invention. In one exemplary embodiment, the pliable valve body is made from a TPE material and is over-molded to the rigid body skeleton 92 of FIG. 6. From the proximal end or top 146, the valve body 94 comprises a sloped entrance 38 comprising an internal lip 148 and an external lip 150. The internal lip 148 extends inwardly relative to the internal wall surface of the inlet section 152 and the external lip 150 extends outwardly relative to the external wall surface of the inlet section 152. When over-molded to the skeleton shell 92, the external lip 150 overlays the top perimeter 66 of the inlet section 96 of the skeleton shell and the internal lip 148 forms a constriction or a reduced section of the inlet opening 154. The internal lip 148 is configured to trap or prevent the plug from dislodging from the inlet section 152 of the valve, as further discussed below. The combination inlet section 96 of the skeleton shell 92 and the inlet section 152 of the valve body 94 form the luer inlet of the valve 88.

A plurality of asymmetrical hour-glass like baffles 156 are formed in the interior cavity 70 of the valve body 94. In one exemplary embodiment, four evenly-spaced apart baffles 156 are provided in the interior cavity 70. Each baffle 156 comprises a wide upper baffle section, a funnel mid-section and a narrow lower baffle section. Looking at a side view of one of the baffles 156, the baffle 156 slopes at the funnel section to form a ramp. Thus, the smallest dimension or opening of the interior cavity 70 when the valve is in the relaxed or first position is at the point where the four funnel sections of the four baffles 156 are located. A plurality of gaps 158 are formed between the baffles 156. The gaps 158 function as flow channels for flow coming from the inlet section 152 or towards the inlet section 152, which depends on whether a sample is taken or a fluid is injected through the valve.

Similar to the baffles 156 located inside the interior cavity 70, the valve body 152 is shaped like an asymmetrical hourglass just below the inlet section 152. The central or mid section of the valve body 94 comprises an upper valve body section 160, a funnel mid-section 162, and a lower valve body section 164. As is readily apparent, the upper valve body section 160 tapers radially inwardly towards the central axis of the valve whereas the lower valve body section 162 tapers outwardly away from the central axis of the valve. The funnel or mid-section 162 is positioned at the transition of the upper section 160 and lower valve body section 164. In one exemplary embodiment, the funnel mid-section 162 and the tip of the lower baffle sections of the baffles 156 are located at approximately the same general position on the valve body 94.

Just distal or below the lower valve body section 164 is a tapered base section 166. The tapered base section 166 tapers radially inwardly from the tip of the lower valve body section 164 and occupies a part of the annular opening 138 of the skeleton shell 92, near the deflection post 132, leading to the elongated port 106. The tapered base section 166 forms around the two thin profile ribs 136 during the over-molding step.

An outlet port or section 116 is integrally formed to the tapered base section 166. The outlet port 116 comprises an internal sleeve 170 and an external sleeve 172 defining a groove 174 therebetween. The internal sleeve 170 functions as an outlet liner for the outlet port 113. The groove 174 is configured to receive the elongated port 106 while the internal sleeve 170 and the external sleeve 172 are configured to line the port 106, at least in part, both internally and externally. Together, the outlet port section 116, the elongated port 106, and the shroud 104 form the male luer connector 113 for the valve 88.

Figure 8:
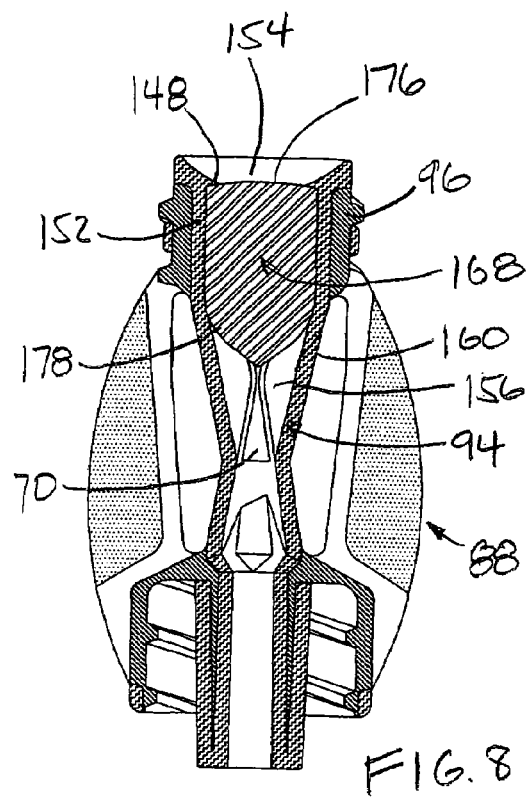
FIG. 8 is a semi-schematic cross-sectional side view of the valve of FIG. 5 with a plug in a first or ready to use position.

Turning now to FIG. 8, a cross-sectional side view of the valve 88 of FIG. 5 is shown. In the valve first position shown, a plug 168 is positioned at the inlet section 152 of the valve with the top surface 176 of the plug pushed against the internal lip 148 of the inlet section. The plug 168 is installed in the interior cavity 70 of the valve by coating the plug with a lubricant, such as medical grade silicone, and then forcing the plug through the opening 154. The plug 168 may be urged towards the inlet section 152 and against the lip 148 by the elasticity of the valve body 94. More particularly, because the plug 168 has a cross-sectional area that is larger than the cross-sectional area of the valve body 160, the valve body 160 squeezes on the plug 168. Due to the tapered upper body section 160 of the valve body 94 and the tapered bottom section 178 of the plug 168, a pair of component forces is produced that urges the plug 168 proximally. In one exemplary embodiment, the plug 168 and the inlet section 152 incorporate a standard Luer to Luer engagement.

Figure 9:
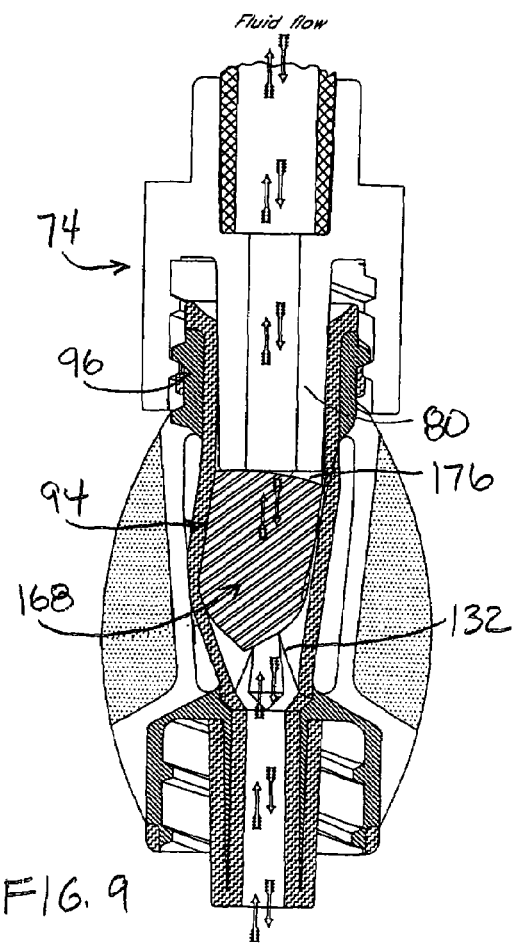
FIG. 9 is a semi-schematic cross-sectional side view of the valve of FIG. 5 with a plug moved to a second or use position by a medical device.

Referring now to FIG. 9, a medical implement 74 is shown connected to the inlet 96 of the valve 88. The luer tip 80 of the medical implement 74 pushes the plug 168 downwardly into the interior cavity 70 of the of the valve body 94. In the process, the plug 168 expands the valve body and is tilted when it contacts the slanted surface 134 of the deflection post 132. The tilted plug 168 creates a gap between the top surface 176 of the plug 168 and the luer tip 80 of the medical implement 74 to provide a flow space for fluid flow flowing either from the medical implement or towards the medical implement, depending on whether fluid is injected through the valve 88 or a sample is drawn through the valve. In a preferred embodiment, the gap is enhanced by incorporating a crown or bulge plug top surface. When the medical implement 74 is subsequently removed, the resilient valve body 92 contracts to return to its original configuration. The contraction produces a contraction force against the tapered bottom section 178 of the plug 168 and pushes the plug proximally until the top surface 176 seats against the internal lip 148 of the inlet section 152. Although not shown, ribs are incorporated in the interior cavity of the valve body to provide fluid flow space or channels.

In an alternative embodiment, the top surface 176 of the plug 168 incorporates grooves or flow channels for providing flow paths between the plug and the male luer tip 80. If incorporated, the deflection post 132 may be eliminated as the plug 168 will not have to tilt to create a flow gap. In yet another alternative embodiment, the gripping fins 114 (FIG. 5) may each incorporate a pyramid-like or rectangular like shape and at the distal section thereof wraps around the periphery of the outlet shroud 104 to either supplement or replace the gripping pads 115.

Figure 10:
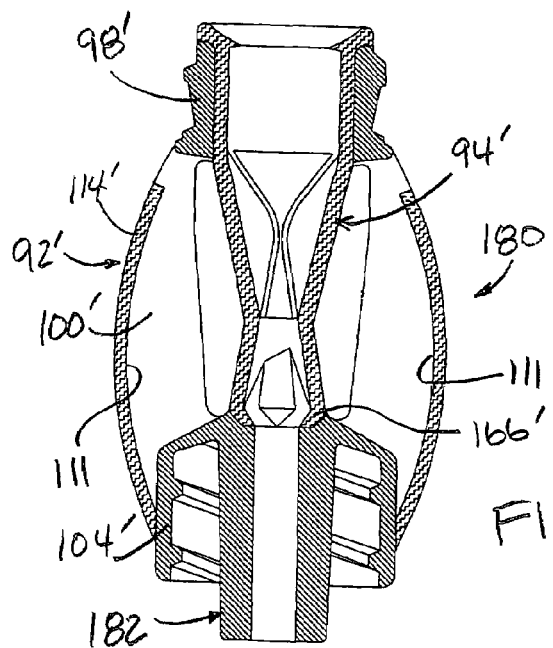
FIG. 10 is a semi-schematic cross-sectional side view of another alternative needleless access port valve provided in accordance with aspects of the present invention; shown without a plug for clarity.

FIG. 10 is a semi-schematic cross-sectional side view of yet another alternative valve embodiment provided in accordance with aspects of the present invention, which is generally designated 180. The valve 180 is shown without a plug for clarity and is useable with any number of plugs described elsewhere herein. The present valve 180 is similar to the valve 88 of FIGS. 5-9 with the following few exceptions. The skeleton shell 92' incorporates a complete male luer connector 182 and not a partial connector comprising only the elongated port 106 and a separate liner. Thus, the pliable valve body 94' terminates at the tapered base section 166' and does not include an outlet liner section 116. Finally, the gripping fins 114' and the guide ribs 100' have also been modified. In the present embodiment, the guide ribs 100' are formed with a recessed receiving section 111 extending from approximately just distal of the external threads 98' to a section located on the outer shroud 104. The recessed receiving section 111 allows the gripping fins 114' to be over-molded and received thereto. In one exemplary embodiment, both the guide ribs 100' and the gripping fins 114' incorporate a shape of a sail having an apex near the external threads 98' and widen while curving to form the outer contour of the valve as they extend distally towards the shroud 104'.

FIG. 11 is a semi-schematic cross-sectional side view of yet another alternative valve embodiment 184 provided in accordance with aspects of the present invention. Like the valves discussed elsewhere herein, the valve 184 of the present embodiment incorporates a rigid thermoplastic skeleton shell 186 and a pliable valve body 188 preferably made from a TPE material. In one exemplary embodiment, the skeleton shell 186 includes integrally formed inlet section 96, guide ribs 189, and male luer connector 190. The guide ribs 189 incorporate a shape of a sail having an apex near the external threads 98 and widen while curving as they extend distally towards the shroud 104. The pliable valve body 188 includes a valve core 192 and separately formed gripping fins 194. The valve core 192 incorporates a configuration which tapers inwardly as it extends downwardly from the inlet section 152 towards the outlet section 80. The inward taper facilitates positioning of the plug at the inlet.

In one exemplary embodiment, a centering post 196 is formed on a base surface 198 of the outlet shroud 104. The centering post 196 comprises an opening 201 in communication with the lumen 200 of the male luer 80. A deflection post 132 is formed proximate the centering post 196 and preferably superjacent to the centering post. The deflection post 132 is attached to the centering post 196 by a pair of thin-profile ribs 136. The deflection post 132 bisects the opening 201 to form two flow channels or paths for fluid flow.

In one exemplary embodiment, the pliable valve body 188 is over-molded to the skeleton shell 186. The valve body 188 includes an inlet section 152 comprising an internal lip 148 and an external lip 150, as previously discussed with reference to FIGS. 7 and 8. At the distal end, a base seal 202 forms around the centering post 196 and seals the valve body to the male luer connector 190.

To facilitate urging the plug 168 into a closed position and to provide flow channels for fluid flow, a plurality of integrally formed baffles 68 are positioned in the interior cavity 70 of the valve body 188. In one exemplary embodiment, four baffles 68 are incorporated. However, 2, 3, or more than four baffles may be incorporated without deviating from the spirit and scope of the present invention. As previously discussed, the baffles 68 have inclined surfaces that form ramps. The ramps 68 and the elasticity of the valve body 188 interact with the tapered bottom section 178 of the plug 168 to urge the plug into a closed position.

Referring now to FIG. 12, a cross-sectional side view of the valve 184 of FIG. 11 is shown in used with a medical implement 74 attached to the inlet section 96 of the valve and the male luer tip 80 of the medical implement 74 forcing the plug 168 downwardly towards the deflection post 132. When the plug 168 contacts the slanted surface 134 of the deflection post 132, the post causes the plug 168 to slant or tilt to create a gap between the top surface 176 of the plug and the opening of the male luer tip 80. The tilt causes a lower portion of the valve core 192 adjacent the tapered bottom section 178 of the plug and an upper section 179 of the valve core 192 opposite the lower section to bulge outwardly. The bulging of the valve core 192 creates a tension force that pushes against the plug 168 and subsequently pushes the plug upwardly or proximately towards the inlet opening 154 when the medical implement 74 is removed and the valve core contracts. Thus, the valve 184 in the present embodiment has a plug 168 that is moveable from a first position to a second position by a downward force generated by a medical implement and moveable from the second position to a first position after the downward force is removed by the contraction force of the resilient valve body.

Figure 13:
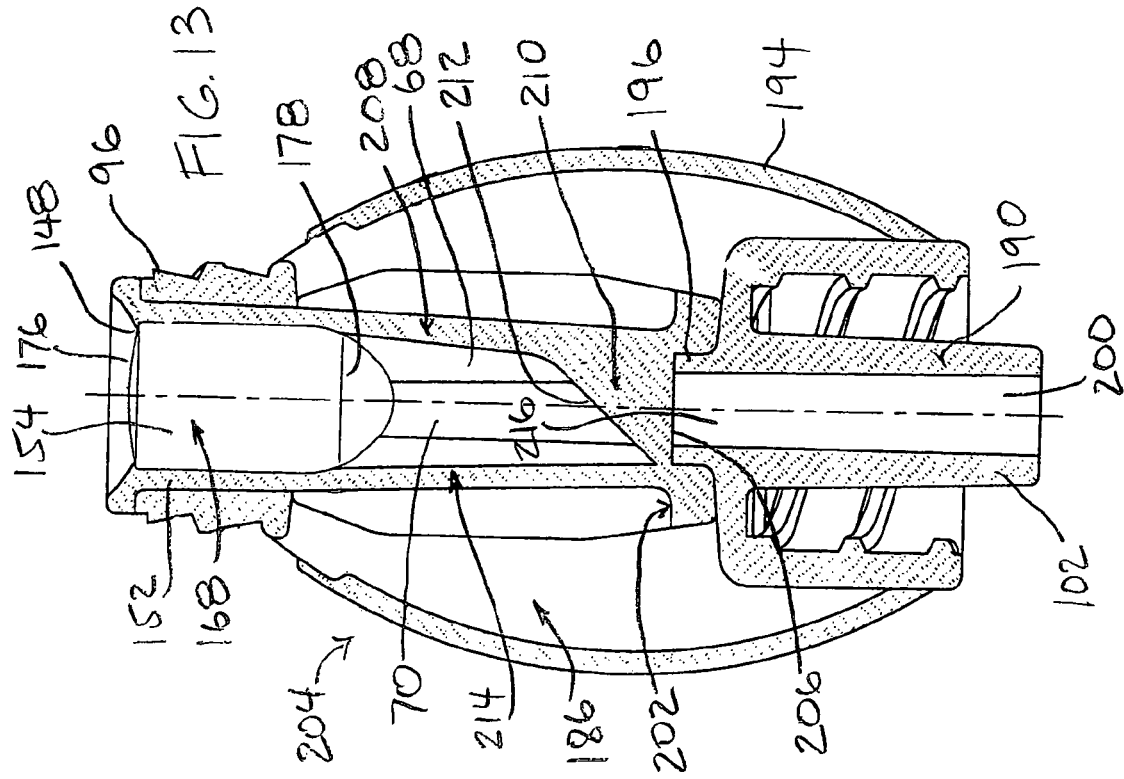
FIG. 13 is a semi-schematic cross-sectional side view of yet another alternative needleless access port valve provided in accordance with aspects of the present invention.

FIG. 13 is a semi-schematic cross-sectional side view of yet another alternative valve 204 provided in accordance with aspects of the present invention. In the present embodiment, a skeleton shell 186 similar to that incorporated in the valve of FIG. 11 is incorporated. However, an integrally formed deflection post 132 is not incorporated superjacent the centering post 196. A pliable valve body 208 comprising an inlet section 152 and a base seal 202 similar to the pliable valve body 188 of FIG. 11 is incorporated in the present embodiment. A deflection rib 210 comprising a slanted edge 212 is incorporated near the base seal 202. The deflection rib 210 is formed by integrally molding a generally flat TPE section in the interior cavity 70. The deflection rib 210 bisects the opening 216 of the valve body 208 at the base seal 202. Thus, the interior cavity 70 of the valve body 208 is in fluid communication with the lumen 200 of the male luer connector 190 and is partially obstructed by the deflection rib 210.

The valve 204 of the present embodiment operates by attaching a medical implement to the inlet section 96 and pushing the plug 168 from a first position downwardly to a second position. As the plug 168 moves downwardly, the plug stretches and expands the valve body 208 due to the relative cross-sectional area of the plug and of the valve body. As the plug travels distally, the lower base section 178 of the plug contacts the deflection rib 210 and tilts. The tilt creates a gap between the top surface 176 of the plug and the male luer tip of the medical implement. The gap acts as a fluid flow space for fluid flowing from either the medical implement, if fluid is to be injected through the valve from the medical implement, or towards the medical implement, if fluid is to be drawn from the outlet section 102 into the medical implement.

When the medical implement is subsequently removed from the inlet section 96 of the valve, the valve body 214 contracts to return to its first position. The contraction force generated by the valve body 214 imparts a pair of component forces on the plug 168 and pushes the plug from the second position towards the first position. The plug's proximal travel is delimited by the internal lip 148, which partially occludes the inlet opening 154 of the valve 204.

In an alternative embodiment, the plug 168 may include ridges or projections to create flow paths along at the top surface 176 of the plug. If incorporated, the plug 168 would not have to tilt and the deflection rib 210 may be omitted. In another alternative embodiment, the threaded inlet section 96 incorporates vertical channels or slots that extend along a lengthwise direction with the central axis of the valve 204 for providing pressure relief for the plug 168. As previously discussed, the pressure relief may be desired as the plug 168 and the inlet has a slight interference fit.

Figure 14:
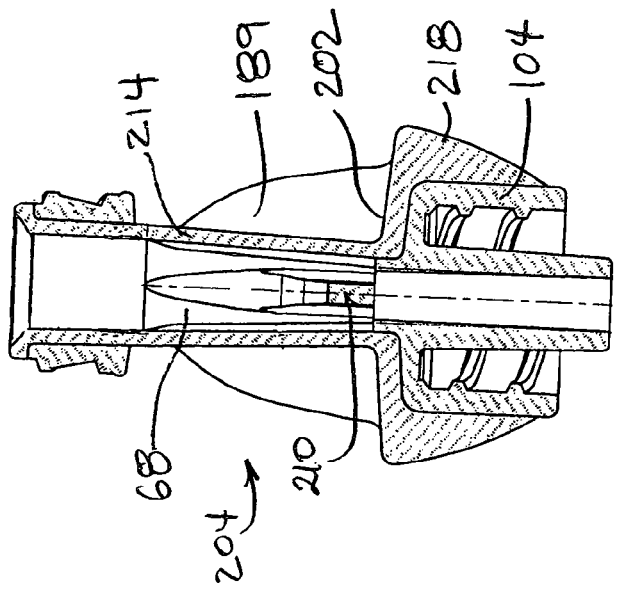
FIG. 14 is a semi-schematic cross-sectional side view of the valve of FIG. 13, shown without a plug.

FIG. 14 is a cross-sectional side view of the valve 204 of FIG. 13, shown without the plug 168. The base seal 202 is over-molded to the outlet shroud 104 by extending the seal between the two guide ribs or guide columns 189 and then downwardly over at least a portion of the outlet shroud 104. Each downward portion 218 extends and intersects two adjacent gripping fins 194 (FIG. 13). In one exemplary embodiment, the downward portions 218 are integrally formed with the two gripping fins 194.

Figure 15:
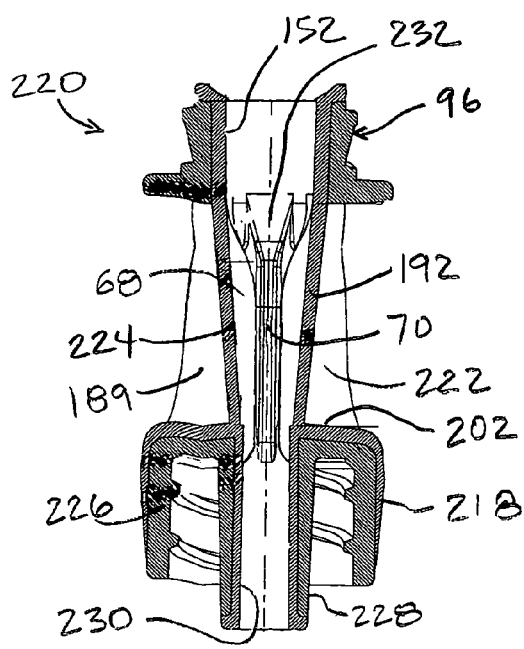
FIG. 15 is a semi-schematic cross-sectional side view of still yet another alternative needleless access port valve provided in accordance with aspects of the present invention, shown without a plug.

FIG. 15 is a cross-sectional side view 220 of an alternative valve provided in accordance with aspects of the present invention. Like the valves discussed elsewhere herein, the valves in the present embodiment comprises a rigid thermoplastic skeleton shell 222 and a pliable valve body 224, preferably made from a TPE material. The shell 222 comprises an inlet section 96, a pair of guide ribs 189, and a male luer connector 226 comprising a male luer nozzle 228 configured to receive a male luer liner 230. The male luer nozzle 228 and the male luer liner 230 together form a male luer tip.

In one exemplary embodiment, the pliable valve body 224 comprises an inlet section 152, which forms a liner for the inlet section 96 of the shell 222, a valve core 192 that expands and contracts to accommodate a plug and that urges the plug into a closed position, an outlet section 230 comprising the liner, and a base seal 202 comprising a downward seal section 218.

In one exemplary embodiment, a plurality of baffles 68 are incorporated in the central cavity 70 of the valve core 192. The baffles 68 are spaced-apart from one another and form flow channels therebetween. In one exemplary embodiment, the baffles 68 each incorporates an inclined section 232 that incline from the interior surface of the interior cavity 70. The baffles 68 together form a funnel-like shape for receiving a tapered lower section of a plug (See, e.g., plug 168 of FIG. 12). The baffles 68 also function to urge the plug into a first ready position.

Figure 16:
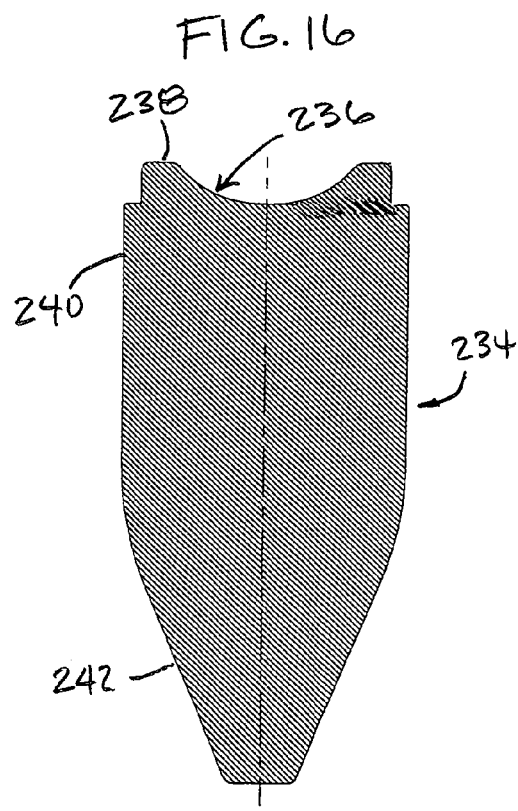
FIG. 16 is a semi-schematic cross-sectional side view of an exemplary plug provided in accordance with aspects of the present invention, which is usable with any number of needleless access port valves described elsewhere herein.

FIG. 16 shows a cross-sectional side view of a plug provided in accordance with aspects of the present invention, which is generally designated 234. The plug 234 comprises a top section 236 which comprises a plurality of protrusions 238, an intermediate section 240, and a lower tapered section 242. In one exemplary embodiment, the intermediate section 240 is generally cylindrical in configuration. In a preferred embodiment, the intermediate section 240 comprises a luer taper sized to create a standard Luer to Luer engagement with the corresponding inlet section.

The lower tapered section 242 preferably incorporates a greater draft angle than the taper on the intermediate section 240. In one exemplary embodiment, the respective draft angle, diameter, and length of the intermediate section 240 and lower section 242 are such that they permit the plug 234 to move from a first position within an interior cavity of a valve to a second position within the interior cavity of the valve and then subsequently return to the first position. In one exemplary embodiment, the plug is sized such that it seals, i.e., close off fluid communication, the inlet opening of the valve.

Figure 17:
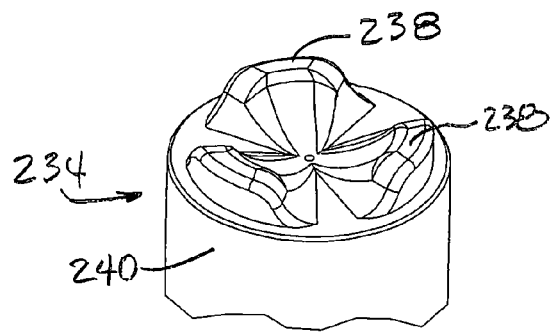
FIG. 17 is a semi-schematic partial perspective view of the plug of FIG. 16.

Referring now to FIG. 17, a semi-schematic partial perspective view of the plug 234 of FIG. 16 is shown. In one exemplary embodiment, three protrusions 238 are shown. The top surface of each protrusion 238 comprises a generally flat surface for contracting and receiving the impact or downward force of the luer tip of a medical implement. Low regions in between the protrusions 238 function as flow paths or channels for permitting flow flowing from either a medical implement or towards the medical implement. As is readily apparent to a person of ordinary skill in the art, when the plug 234 is used with any of the various valves described elsewhere herein, tilting means for tilting the plug may be omitted. However, the plug 234 may optionally be used with the tilting means.

FIG. 18 is a cross-sectional side view of yet another valve embodiment 244 provided in accordance with aspects of the present invention. The valve 244 incorporates a rigid thermoplastic skeleton shell 222 and a pliable valve body 245, preferably made from a TPE material. The skeleton shell 222 is similar to the shell 222 of FIG. 15 in that it comprises an inlet section 96, integrally formed guide ribs 189, and integrally formed male luer connector 226 comprising an enlarged male tip nozzle 228 adopted for receiving a tip liner 230 of the pliable valve body 245. In one exemplary embodiment, the pliable valve body 245 comprises a combination valve seat 246 and tapered body section 248. The valve seat 246 is formed by providing a sharp reduction in diameter at a lower section of the inlet section 152 of the pliable valve body 245. The sharp reduction in diameter produces a reduced diameter opening 250 at the transition between the upper inlet section 152 and the tapered body section 248.

When a plug 234 is inserted into the inlet section 152 of the valve, the lower tapered section 242 of the plug rests against the valve seat 246. However, in one exemplary embodiment, the plug 234 does not seal against the valve seat 246. Among other things, a plurality of baffles 252 are incorporated near the valve seat 246. In one exemplary embodiment, four baffles 252 are incorporated with each baffle originating from the inlet section 152, extending through the valve seat 246, and terminating at the tapered body section 248. The baffles 252 form flow channels therebetween and the seat 246 therefore does not provide a complete seal against the plug 234. The seal for sealing the inlet opening 154 of the valve 244 from the interior cavity 70 of the valve is provided by the interference fit between the plug 234 and the inlet section 152. Portions of the baffles 252 at the tapered body section 246 may vary in thickness from the surface of the interior cavity 70. The variation is provided to facilitate urging the plug, as discussed further below.

The valve 244 is configured to receive a first medical implement (not shown) at the inlet section 96 and a second medical implement (not shown) at the male luer connector 226. When the first medical implement is engaged to the inlet section 96, the plug 234 is pushed from the position shown, i.e., the first position, distally towards the tapered body section 248 of the interior cavity 70, i.e., the second position. When the plug 234 is moved to the second position, fluid is transferable between the first medical implement and the second medical implement by flowing through the interior cavity 70. Upon removal of the first medical implement, the tapered body section 248 and the valve seat section 246 of the pliable valve body 245 urge the plug 234 proximally towards the first position.

As discussed with other guide ribs, the guide ribs 189 incorporated herein may vary in shape and configuration provided they are sufficiently rigid to maintain a substantially constant gap between an upper flange 35 and a lower flange when the plug 234 moves between a first position and a second position. In the present embodiment, the lower flange can be the base surface 198 of the shroud 104. As is readily apparent to a person of ordinary skill in the art, the two markers for keeping or maintaining constant by the guide ribs 189 may be other than the upper flange 35 and the base surface 198. In other words, two different reference points may be used.

FIG. 19 is a semi-schematic cross-sectional view of an alternative valve embodiment 254 provided in accordance with yet other aspects of the present invention. The valve 254 comprises a rigid thermoplastic outer shell 222 and a pliable valve body 245, much like the valve shown and described with reference to FIG. 18. In the present embodiment, a plurality of baffles 256 are incorporated in the interior cavity 70 beginning at the inlet section 152 and extending into the tapered body section 248. Each baffle 256 comprises a first section 257 of substantially uniform thickness, and a second section 258 of different thickness.

FIG. 20 is a semi-schematic cross-sectional view of yet another alternative valve embodiment provided in accordance with aspects of the present invention, which is generally designated 260. The valve 260 is similar to the valves shown and described with reference to FIGS. 18 and 19 in that it incorporates a rigid thermoplastic outer shell 222 and a resilient pliable valve body 262. The pliable valve body 262 tapers inwardly from a proximal point on the valve body to a distal point on the valve body. As previously discussed, the taper interacts with a plug 234 by stretching or bulging outwardly when a downward force is exerted on the plug and then contracting inwardly to push the plug back to its first position when the downward force is removed.

A plurality of spiraled ribs 264 are incorporated in the central cavity 70 of the valve body 262. In an exemplary embodiment, each rib extends axial and radially from a proximal position in the interior cavity to a distal position in the interior cavity. In a preferred embodiment, four spiraled ribs 264 are incorporated with each rib originating at a same proximal position inside the cavity and terminating at a same distal position in the cavity as the adjacent rib. However, the number of ribs and the originating and terminating points can vary. Preferably, the ribs 264 are placed such that when the plug 234 is moved from a first position to a second position, flow channels are exposed between the exterior surface of the plug and the interior surface 266 of the interior cavity to permit fluid communication between the inlet opening 268 of the valve and the outlet opening 270 of the valve.

FIG. 21 is a semi-schematic side view of an alternative needleless access port valve 272 provided in accordance with aspects of the present invention. The valve 272 may be constructed in accordance with the valves described elsewhere herein, such as with the valves of FIGS. 13-15 and 18-19. Thus, in one exemplary embodiment, the valve shown incorporates a rigid skeleton shell 222 and a resilient and pliable valve body 274. The skeleton shell 222 includes a rigid inlet section 96, guide ribs 189, and part of the luer connector 226. The valve body 274 includes an inlet liner 152, a flexible body section 276 and a tip liner 230. Four reinforcing ribs or gussets 278 are shown on the guide ribs 189 for strengthening the upper flange 35.

In one exemplary embodiment, a plurality of cantilever arms 280 are incorporated with the skeleton shell 222. In a preferred embodiment, four cantilever arms 280 are incorporated. The cantilever arms 280 each comprises an attachment point 282 and an active point 284. In one exemplary embodiment, the cantilever arms 280 are attached to the upper flange 35 at their respective attachment points 282. The arms 280 extend distally and radially inwardly to create pivoting points proximate their respective attachment points. At the active points 284, the arms 280 are slightly spaced apart from the exterior surface of the flexible body section 276. However, the arms 280 may contact or be bonded to the exterior surface of the flexible body section 276 without deviating from the spirit and scope of the present invention.

When the valve 272 is in use by moving the plug (not shown, See, e.g., FIG. 19, plug 234) from a first position to a second position with a medical implement, the plug expands the flexible body section 276, which in turn pushes on the arms 280 and flexes the arms radially outwardly. When the medical implement is subsequently removed, the flexible body section 276 contracts, as previously discussed, and the cantilever arms 280 bias radially inwardly to further facilitate moving or returning the plug to its first position. In one exemplary embodiment, two gaps 279 on the inlet section 96 are incorporated to facilitate movement of the plug by permitting the pliable inlet section to expand into the two gaps.

FIG. 22 is a semi-schematic cross-sectional side view of yet another alternative needleless access port valve 284 provided in accordance with aspects of the present invention. In one exemplary embodiment, the valve 284 incorporates a rigid skeleton shell 286 and a resilient and pliable valve body 288, similar to other valves discussed elsewhere herein. The rigid skeleton shell 286 includes an inlet section 290, two guide ribs 292, and a male luer connector 226 comprising a male luer nozzle 228 configured to receive a male luer liner 230. The male luer nozzle 228 and the male luer liner 230 together form a male luer tip. In one embodiment, the inlet section 290 comprises external threads 294, a top flange 296, an interior surface 298 defining an interior cavity, and a tapered inlet end 300. Preferably, the interior surface is formed with a luer taper and is configured to mate with and sealed by the taper on a plug 234.

The flexible components in the present valve embodiment include an inlet seat 302 co-molded to the inlet section 290, a flexible valve body 288, and outlet liner 230, and a gripping liner 304. As is readily apparent from the FIG. 22 valve, the gripping liner 304 and the guide ribs 292 incorporate arcuate surfaces for enhanced gripping capability.

A plurality of baffles 306 adorn the interior cavity 70 of the valve body 288. In one exemplary embodiment, four baffles 306 originating from approximately just distal of the flange 296 and extending the length of the valve body to the outlet liner 230 are incorporated. When the plug 234 is moved from a first position to a second position, the baffles 296 provide flow gaps or channels for fluid flow through the valve, i.e., for fluid communication between the inlet opening 268 and the outlet opening 270.

As previously discussed, when the plug 234 is moved to a second position by a medical implement, the plug 234 expands the valve body 288 due to the relative girth of the plug as compared to the opening dimension of the interior cavity 70 of the valve body. When the medical implement is subsequently removed, the resilient valve body contracts and exerts a pair of component forces on the tapered plug 234 to move the plug distally. The plug's movement is further facilitated by the presence of the stabilizing rings 308. In one exemplary embodiment, two stabilizing rings 308 are incorporated to provide added resilient material or thickness. In a preferred embodiment, the two stabilizing rings 308 are integrally formed with the valve body 288.

FIG. 23 is a semi-schematic side view of an alternative valve 310 provided in accordance with aspects of the present invention. The valve comprises a rigid skeleton shell 312 and any number of pliable valve body disclosed elsewhere herein, such as the valve body 192 of FIG. 15. The skeleton shell 312 includes an inlet section 96, a top flange 35, and a male luer connector 314 having a male luer nozzle 228. The male luer nozzle 228 cooperate with a luer liner 230 to form a male luer tip.

The reinforcing ribs 189 in the present embodiment interconnect with a shroud section 316 that forms part of the female threads for the male luer connector at the valve outlet. A pair of openings 318 are incorporated between the reinforcing ribs 189 for access and for expansion room for the valve body 192. In one exemplary embodiment, a radius edge 320 is incorporated at each opening 318.

FIG. 24 is a semi-schematic side view of the valve 310 of FIG. 23.

Although limited embodiments of the needleless access valve assemblies and their components have been specifically described and illustrated herein, many modifications and variations will be apparent to those skilled in the art. For example, the various valves may incorporate luer-slips rather than luer threads, both the plug and the pliable valve body may be made from a two-part self-lubricating silicone, the material selected could be opaque or semi-opaque, the various baffles can change shape, size, position, etc. Furthermore, it is understood and contemplated that features specifically discussed for one valve embodiment may be adopted for inclusion with another valve embodiment, provided the functions are compatible. For example, a plug with a tail may be used in another embodiment shown with a plug not having a tail. Another example includes substituting the shape or contour of the guide ribs from one valve embodiment with the guide ribs of another valve embodiment. Accordingly, it is to be understood that the valve assemblies and their components constructed according to principles of this invention may be embodied other than as specifically described herein. The invention is also defined in the following claims.

What is claimed is:

1. A needleless access port valve comprising
a valve body having an interior surface and an exterior surface, the exterior surface further comprising a top wall aligned perpendicular to a central axis of the valve body and a side wall aligned non-perpendicular to the central axis and at an angle to the top wall, the top wall and the side wall both being exposed to ambient atmosphere, said valve body comprising a continuous wall surface along a radial direction, an inlet, an outlet, a main channel about the central axis between the inlet and the outlet, and
a plug disposed in the main channel defined by the interior surface of the valve body and has sections that contact sections of the interior surface of the valve body, all of said sections of the plug that contact the interior surface of the valve body being slidable inside the main channel and movable relative to the sections of the interior surface of the valve body that they contact in sliding from between a first position and a second position for controlling fluid communication between the inlet and the outlet, the plug comprising an upper end and a lower end comprising a tapered section;
wherein the continuous wall surface, including the exterior surface of the valve body, flexibly bends inwardly towards the central axis when the plug is in the first position such that a cross-sectional dimension of the valve body is less than a cross-sectional dimension of the inlet; and wherein the continuous wall surface, including the exterior surface of the valve body, flexibly bends outwardly away from the central axis and contacting the tapered section when the plug is in the second position.

2. The needleless access port valve of claim 1, further comprising a rigid skeleton shell.

3. The needleless access port valve of claim 1, wherein the top wall of the valve body is fixed in an axial direction and the plug moves away from the top wall in moving to the second position.

4. The needleless access port valve of claim 1, wherein the plug and the inlet is in a Luer to Luer engagement.

5. The needleless access port valve of claim 1, further comprising a plurality of baffles located in the main channel.

6. The needleless access port valve of claim 5, wherein the plurality of baffles comprise four baffles defining four flow paths.

7. The needleless access port valve of claim 1, wherein the plug comprises a top surface and wherein the top surface comprises a plurality of projections.

8. The needleless access port valve of claim 1, wherein the valve body is made from a thermoplastic elastomer (TPE) material.

9. The needleless access port valve of claim 8, wherein the TPE is a copolyamide thermoplastic elastomer.

10. The needleless access port valve of claim 1, wherein the valve body is over molded to a rigid shell and wherein the rigid shell comprises a threaded collar and a threaded inlet section.

11. The needleless access port valve of claim 1, further comprising a plurality of baffles positioned, at least in part, inside the main channel, and wherein the plurality of baffles each extends axially and radially from the inlet towards the outlet.

12. A needleless access port valve comprising a valve body defining an interior cavity, the valve body having an inlet sized to receive a medical implement when the medical implement is inserted into the inlet to open the valve, and an outlet; a plug disposed in the interior cavity of the valve body and movable within the interior cavity between a first position and a second position for controlling fluid communication between the inlet and the outlet, said inlet and outlet of the body being in fixed relative axial position in both the plug first and second positions,
said plug comprising a top surface having a solid core positioned proximate the inlet for forcing fluid to flow around the plug and a valve body section comprising a flexible wall; wherein the flexible wall expands outwardly to accommodate the plug when the plug moves to the second position inside the valve body and away from the inlet.

13. The needleless access port valve of claim 12, further comprising a rigid skeleton shell.

14. The needleless access port valve of claim 13, wherein the valve body is over molded to the rigid skeleton shell.

15. The needleless access port valve of claim 12, wherein the plug comprises a upper section and a lower section and wherein the lower section comprises a taper.

16. The needleless access port valve of claim 15, wherein the flexible wall contracts against the taper lower section to push the plug back to the first position.

17. The needleless access port valve of claim 12, wherein the valve body comprises an exterior surface and an interior surface, and wherein the exterior surface is exposed to ambient atmosphere.

18. The needleless access port valve of claim 12, further comprising a plurality of baffles positioned in the interior cavity of the valve body.

19. The needleless access port valve of claim 12, wherein the valve body is made from a TPE material.

20. The needleless access port valve of claim 19, wherein the TPE is a copolyamide thermoplastic elastomer.

21. The needleless access port valve of claim 12, wherein the plug moves from the second position to the first position without a resilient spring.

22. A needleless access port valve comprising
a valve body defining an interior cavity including a wall, an inlet having a continuous opening and sized to surround a medical implement when the medical implement is inserted into the inlet, and an outlet having an annular opening; a plug disposed in the interior cavity of the valve body and slidable within the interior cavity between a first position and a second position for controlling fluid communication between the inlet and the outlet;
wherein the plug comprises a solid top surface, which is positioned proximate the inlet of the valve body in the first position, for forcing fluid to flow around the top surface and around a side exterior surface of the plug;
wherein the wall contracts to move the plug from the second position to the first position, and the plug in the first position being further apart from the outlet than when in the second position.

23. The needleless access port valve of claim 22, further comprising a rigid skeleton shell having spaced apart rigid structures defining a gap therebetween.

24. The needleless access port valve of claim 22, wherein the plug comprises an area of a larger cross-sectional dimension nearer the inlet than an area of cross-section nearer the outlet.

25. The needleless access port valve of claim 22, wherein the valve body is made from a TPE material.

* * * * *

UNITED STATES PATENT AND TRADEMARK OFFICE
CERTIFICATE OF CORRECTION

| | | |
|---|---|---|
| PATENT NO. | : 7,510,545 B2 | Page 1 of 1 |
| APPLICATION NO. | : 11/055285 | |
| DATED | : March 31, 2009 | |
| INVENTOR(S) | : Peter W. Peppel | |

It is certified that error appears in the above-identified patent and that said Letters Patent is hereby corrected as shown below:

In column 4, line 46, delete "state" and insert -- state. --, therefor.

In column 19, line 2, in Claim 15, delete "a upper" and insert -- an upper --, therefor.

Signed and Sealed this

Twenty-fifth Day of May, 2010

David J. Kappos
*Director of the United States Patent and Trademark Office*